US00PP09039P

United States Patent [19]

Larson

[11] Patent Number: Plant 9,039

[45] Date of Patent: Jan. 10, 1995

[54] TABLE GRAPE VARIETY NAMED LARSON B-36

[76] Inventor: Drake Larson, P.O. Box 355, Thermal, Calif. 92253

[21] Appl. No.: 134,257

[22] Filed: Oct. 8, 1993

[51] Int. Cl.[6] ..... A01H 5/00

[52] U.S. Cl. ..... Plt./47.1

[58] Field of Search ..... Plt. 47.1

*Primary Examiner*—James R. Peyrer

*Attorney, Agent, or Firm*—Christie, Parker & Hale

[57] ABSTRACT

A new and distinct variety of grapevine producing early maturing black seedless table grapes.

3 Drawing Sheets

BACKGROUND OF THE INVENTION

The invention relates to a new and distinct variety of the *vinifera* species which produces early maturing black seedless table grapes.

The new variety is a the result of a cross of two unnamed, unpatented seedlings of my creation and was one of over 800 such seedlings grown near Thermal, Calif. and brought to fruiting, evaluated and asexually reproduced.

The variety of black seedless grape known as 'Beauty' (unpatented) has been considered the earliest fruiting black seedless grape produced for the commerical market. However, the fruit of 'Beauty' is soft and does not hold in storage well. Another commercial variety, 'Fantasy', tends to crack and is low yielding and matures relatively late.

SUMMARY OF THE INVENTION

The new variety, 'Larson B-36', is a more vigorous plant than 'Beauty' and procuces early maturing black seedless grapes which are firmer than 'Beauty'. The new variety is earlier fruiting, more productive and more economical than the variety 'Fantasy', grapes of which also tend to crack. 'Larson B-36' is also suitable for drying into raisins. In addition, no Gibb is required for sizing and the new variety is low-labor intensive compared to the varieties 'Beauty' and 'Fantasy'. 'Larson N-36' grapes are not prone to splitting or cracking and ship well.

It is also to be noted that GA is not applied and may be phytotoxic. The variety "Fantasy" is cane pruned and not as fruitful as the variety "Beauty" which is cordon pruned. The new variety is quadrilateral cordon pruned. "Beauty" is more fruitful than the new variety but the fruits are weaker. The new variety is generally single spurred because of the youth of the plants. Sometimes producing too much fruit may be a disadvantage because it adversely affects the quality of the fruit and because of the additional labor cost necessary to reduce the excess fruit on the plant.

The canopy density is generally about the same for each variety, as is the bark texture. The internode length may vary with fertilizer and water application. The new variety is self-fertilizing. The foilage coloration varies somewhat, depending upon cultural practices and environmental conditions. The leaves of the new variety include three major leaves and three minor leaves. The sinus in similar to the "Flame" seedless and the margins of the leaves are ordinary. The color of the berries is evident from the illustrations accompanying the application.

Despite early production of the berries, as compared to other varieties, raisin production is possible. However, the harvest is generally concluded before raisins are produced. The raisins are slightly darker than for "Thompson" Seedless.

The fruit of the flesh is essentially translucent and colorless but may include slight green and red tones. The adhesion of the skin to the flesh is similar to that of "Thompson" Seedless. The berries are attached to the bunches and pedicles very well for fresh and stored fruit. The seed traces are small and similar to the "Perlette" Seedless and much smaller than the "Flame" Seedless. Juice of the new variety has not been observed.

This new variety differs in several respects from companion new variety identified as "Larson D-12", now known as Mariah, in the subject of application Ser. No. 08/134,258, filed Oct. 8, 1993. Although, the bud breaks of "Larson B-36" is between "Beauty" and "Thompson" Seedless, the bud breaks of "Larson D-12" is similar to the "Beauty" Seedless. The vigor of "Larson B-36" tends to be greater than "Larson D-12" and fruiting occurs somewhat later, e.g., about four days in the desert climate. In addition, "Larson B-36" attains longer growth at maturity than "Larson D-12" and the trunk diameter is larger. The canopy of "Larson B-36" may be denser than the canopy of "Larson D-12" and similar to the canopy density of "Flame" Seedless. The number of berries per cluster is about the same for both varieties, e.g., 60–200. It is generally desirable to leave about 30 to 60 bunches on "Larson B-36" and 30–40 bunches of "Larson D-12."

Among the novel characteristics possessed by this new variety which distinguish it from its parents and all other varieties of which I am aware are its firm, large berries, early fruiting and maturity, improved flavor and absence of splitting. Fruiting is best when plants are spur (two bud) pruned.

Asexual reproduction by rooted cuttings of the new variety as performed in Thermal, Calif. shows that the foregoing and other distinguishing characteristics come true to form and are established and transmitted through succeeding propagations.

BRIEF DESCRIPTION OF ILLUSTRATION

The accompanying illustrations show typical specimens of the vegitative growth and berries of the new variety depicted in color as nearly true as it is reasonably possible to make the same in a color illustration of this character.

In the drawings, one view illustrates a bunch of grape berries of the new variety, another illlustration depicts the vine of the new variety, a third illustration shows the foilage of the new variety and a fourth illustration describes the interior of the berries. The remaining two illustrations show tendrils and growth of the new variety.

DETAILED DESCRIPTION OF THE NEW VARIETY

Parentage: Seedling.

*Seed parent.*—Unnamed seedling.

*Pollen parent.*—Unnamed seedling.

Species: *Vinifera,* black seedless.

The following is a detailed described description of specimens of the new variety grown in Thermal, Calif. in the month of June, 1993. The color terminology used is in accordance with the Royal Horticultural Society Colour Chart (RHSCC), and refers to plate numbers in the aforementioned color chart. Phenotypic expression may vary depending on environmental, climate and cultural conditions. Where general descriptive terms such as average, normal and medium are used, it is intended that characteristics so described are not considered distinguishing.

VINE

A. Size (general: Very vigorous (much more vigorous than 'Beauty').

B. Form: Condor (quadrilateral).

C. Vigor: Very vigorous.

D. Time of sprouting: mid February, in 1993.

E. Productivity: Moderate yielder.

F. Trunk:

(1) *Trunk diameter.*—About 5 cm (at fruiting age) generally round.

(2) *Bark (color).*—Light brown, similar to 'Thompson'.

(3) *Texture.*—Striated similar to 'Thompson', 'Pearlette' and 'Flame'.

G. Canes:

(1) *Size.*—Average.

(2) *Number.*—About 15–20.

(3) *Diameter.*—Average.

(4) *Color.*—Light brown, similar to 'Thompson', 'Pearlette' and 'Flame'.

(5) *Form.*—Varies from plant to plant until mature.

(6) *Nodes (generally).*—Present.

(7) *Nodes (size).*—Medium.

(8) *Internodes (size).*—Average.

(9) *Internode length.*—About 8.5 to 12.2 cm.

(10) *Number of tendrils.*—Normal.

(11) *Tendril thickness.*—Average.

(12) *Tendril length.*—Average.

(13) *Tendril form.*—Straight to mild spiral.

(14) *Tendril texture.*—Average.

H. Flowers:

*Date of bloom.*—Early April, 1993, flowers have stamens and pistils and produce pollen; self-fertilizing, blooming time starts before 'Beauty° and after 'Larson D-12 .

FRUIT

A. Maturity at time of description: End of May, in 1993.

B. Ripening date: Same as maturity earlier than 'Beauty'.

C. Storage quality: Very good for desert; over 3 weeks.

D. Shipping quality: Very good.

E. Cluster:

(1) *General description.*—Loose, long.

)2) *Size.*—General size, weight—about 0.3 to 0.8 kg.

(3) *Length.*—Medium.

(4) *Natural cluster length.*—About 20 cm.

(5) *Cluster form shape.*—Elongated, conical, uniform, loose filled, about 17 to 23 cm long.

(6) *Peduncle.*—Length: About 2.5 to 3.8 cm. Thickness: Average.

(7) *Pedicel length.*—About 0.8 cm.

F. Berry:

(1) *Berry length (natural vines).*—About 2 to 2.4 cm.

(2) *Berry diameter.*—About 1.5 to 1.8 cm.

(3) *Berry weight.*—About 2.5 to 4.5 gm.; average about 3.8 gm.

(4) *Uniformity.*—Very uniform.

(5) *Berry color.*—Black, near to between 183 A and 53 A.

(6) *Bloom.*—Average, similar to 'Thompson' and less than 'Beuaty', more than 'Flame'.

(7) *Skin.*—Thickness: Medium. Texture: Very firm.

(8) *Brush.*—Retained on pedicel.

(9) *Surface bloom.*—Similar to 'Thompson', less than 'Beauty', more than 'Flame'.

G. Flesh:

(1) *Appearance (general).*—Light color, translucent, firm, flesh well attached to skin, better than 'Thompson' and 'Beauty', similar to 'Pearlette'.

(2) *Texture.*—Very firm, berry crisp.

(3) *Flavor.*—Very sweet; slight plum flavor.

(4) *Quality.*—Very good.

H. Seeds: Seedless.

I. Use: Table grape, juice characteristics not determined.

J. Uniqueness: Earlier than existing varieties; shows no signs of cracking or splitting.

FOLIAGE

A. Density: Moderate, less dense than 'Flame', more dense than 'Beauty'.

B. Size of leaf: Between about 5 and 15 cm long from the point of attachment of the leaf petiole to the tip of the leaf, about 2 to 10 inches wide from furthest point of the two widest lobes of the leaf.

Shape: Generally round.

D. Sinus: Similar to 'Thompson' seedless with both deep and shallow lobes, glabrous on top, matte on underside.

E. Margins: Irregularly serrate and coarse.

F. Color: Top surface near RHS 146C to 146D and bottom surface near RHS 146D; leaves fairly absent of anthocyanin.

I claim:

1. A new and distinct black seedless grape plant known as 'Larson B-36', substantially as shown and described.

* * * * *

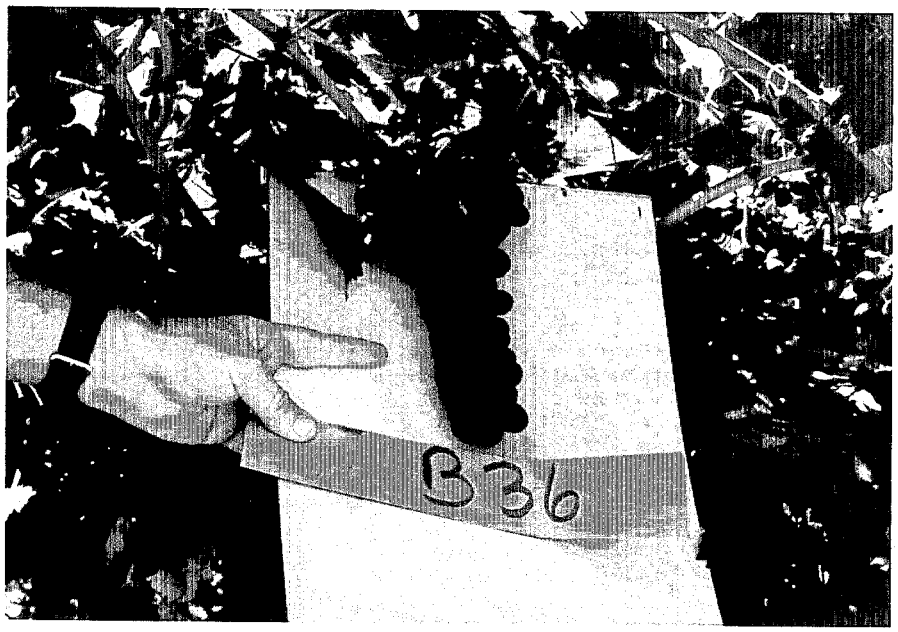
B36
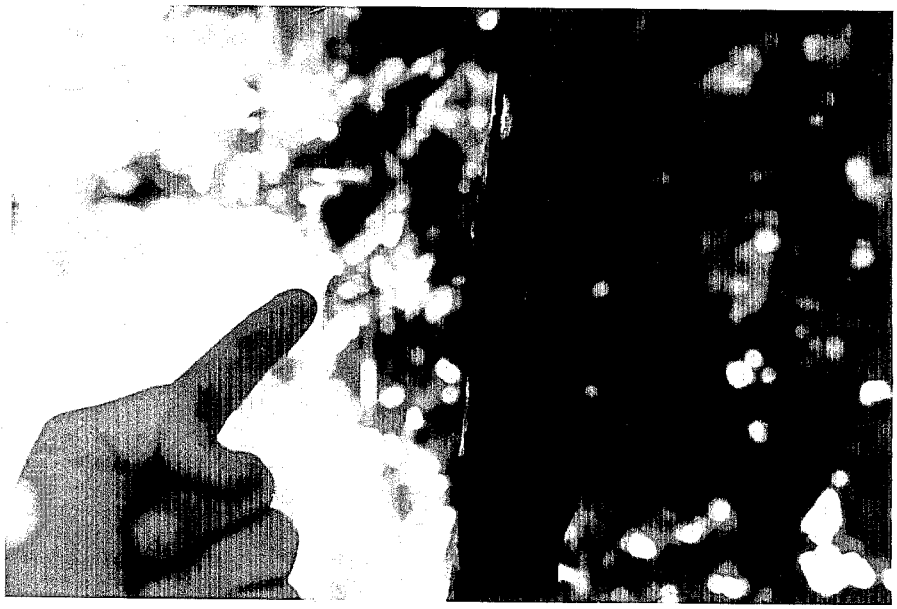

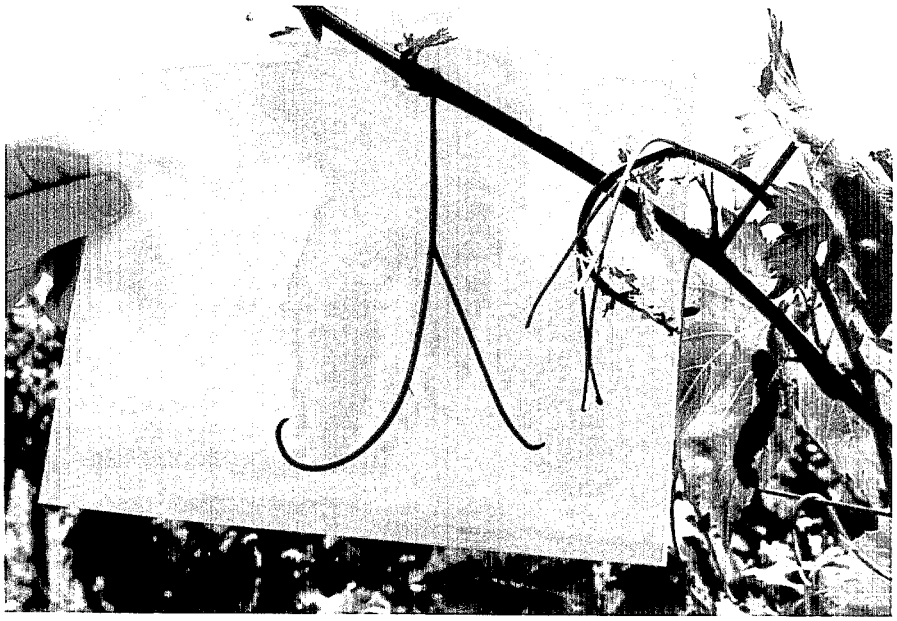
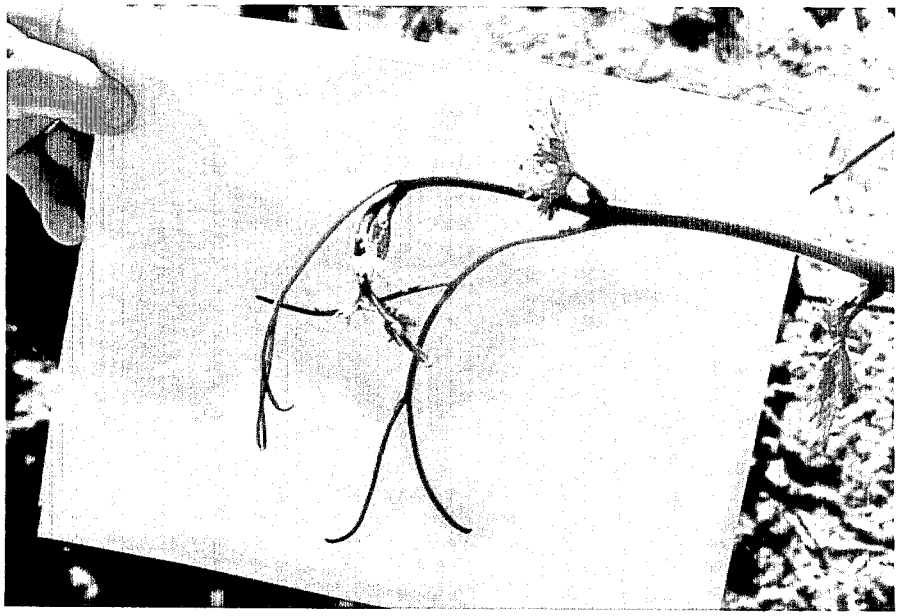

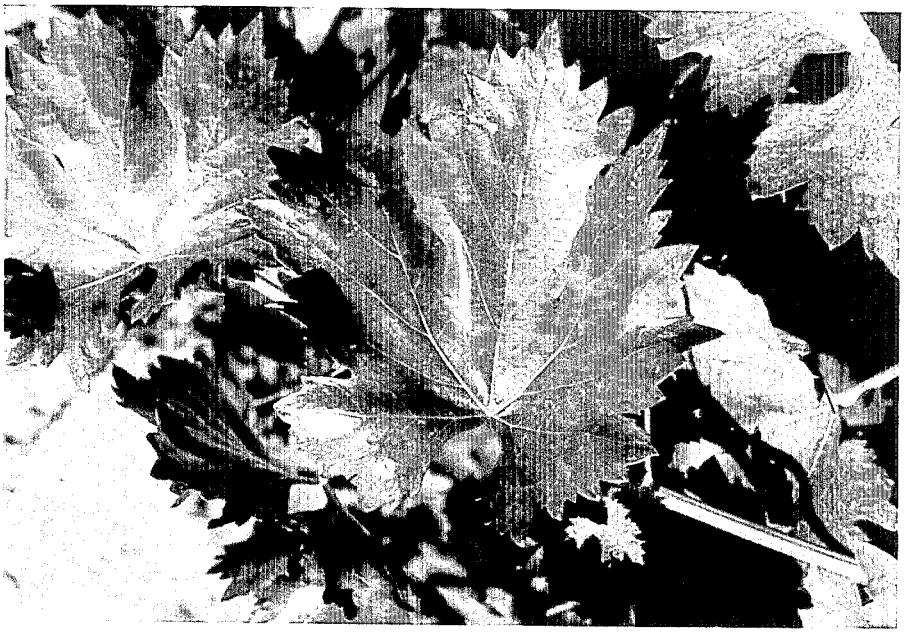
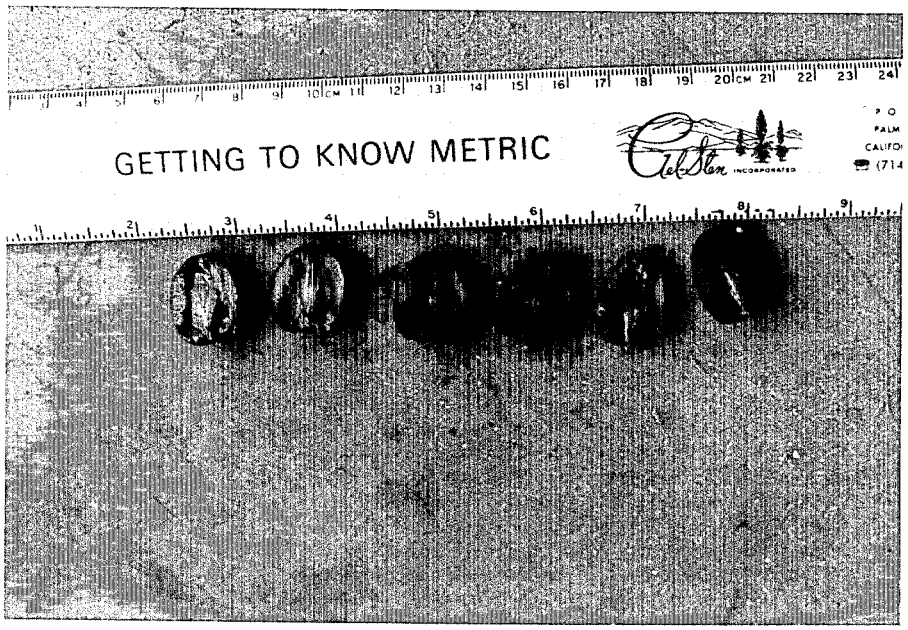
GETTING TO KNOW METRIC